(12) United States Patent
Vähäsöyrinki et al.

(10) Patent No.: US 10,427,292 B2
(45) Date of Patent: Oct. 1, 2019

(54) LINKED MICROMECHANICAL POSITIONING APPARATUS FOR REAL-TIME TESTING AND MEASUREMENT

(71) Applicant: Sensapex Oy, Oulu (FI)

(72) Inventors: Mikko Vähäsöyrinki, Oulu (FI); Markku Vimpari, Oulu (FI)

(73) Assignee: Sensapex Oy, Oulu (FI)

( * ) Notice: Subject to any disclaimer, the term of this patent is extended or adjusted under 35 U.S.C. 154(b) by 0 days.

(21) Appl. No.: 15/765,576

(22) PCT Filed: Oct. 13, 2015

(86) PCT No.: PCT/FI2015/050689
§ 371 (c)(1),
(2) Date: Apr. 3, 2018

(87) PCT Pub. No.: WO2017/064354
PCT Pub. Date: Apr. 20, 2017

(65) Prior Publication Data
US 2018/0272523 A1    Sep. 27, 2018

(51) Int. Cl.
*G05B 1/06* (2006.01)
*B25J 7/00* (2006.01)
(Continued)

(52) U.S. Cl.
CPC ............... *B25J 7/00* (2013.01); *B25J 13/02* (2013.01); *B81B 3/00* (2013.01);
(Continued)

(58) Field of Classification Search
CPC .................................. B21J 7/30; H02K 41/031
(Continued)

(56) References Cited

U.S. PATENT DOCUMENTS 5,677,709 A   10/1997   Miura et al.
7,013,717 B1   3/2006   Struckmeier et al.
(Continued)

FOREIGN PATENT DOCUMENTS

EP   0536827 A1   4/1993
EP   2541300 A1   1/2013
(Continued)

OTHER PUBLICATIONS

European Patent Office, extended European search report of European patent application No. 15906190.2, dated Apr. 18, 2019, 3 pages.
(Continued)

*Primary Examiner* — Erick D Glass
(74) *Attorney, Agent, or Firm* — Berggren LLP

(57) ABSTRACT

The invention relates to a positioning device (120, 154), for example for testing, comprising a micromechanical positioning actuator (130) for causing movement of a probe (150, 151) with respect to a target (110), a positioning controller (145), the positioning controller (145) having an output coupled to the actuator (130) for controlling the movement, and the positioning controller (145) having a steering input (156) for receiving a steering signal to the positioning controller (145), and the positioning controller (145) arranged to control the movement based on the steering signal. The measurement device may have memory for storing positioning control instructions (300). The positioning controller (145) may be arranged to control said movement based on said steering signal and said positioning control instructions (300).

20 Claims, 7 Drawing Sheets

(51) Int. Cl.
*B81B 3/00* (2006.01)
*G01N 33/487* (2006.01)
*G02B 21/32* (2006.01)
*B25J 13/02* (2006.01)
*G01Q 60/44* (2010.01)
*G01Q 70/06* (2010.01)
*G01Q 10/06* (2010.01)
*G01Q 30/02* (2010.01)

(52) U.S. Cl.
CPC . *G01N 33/48707* (2013.01); *G01N 33/48728* (2013.01); *G02B 21/32* (2013.01); *G01Q 10/065* (2013.01); *G01Q 30/02* (2013.01); *G01Q 60/44* (2013.01); *G01Q 70/06* (2013.01)

(58) Field of Classification Search
USPC .......................................................... 318/640
See application file for complete search history.

(56) References Cited

U.S. PATENT DOCUMENTS

| | | | |
|---|---|---|---|
| 2005/0269035 A1 | 12/2005 | Kawakami et al. | |
| 2013/0023052 A1* | 1/2013 | Tanaka | G02B 21/32 |
| | | | 435/461 |
| 2016/0245843 A1 | 8/2016 | Shioda et al. | |

FOREIGN PATENT DOCUMENTS

| | | |
|---|---|---|
| JP | 2002139414 A | 5/2002 |
| JP | 2009202331 A | 9/2009 |

OTHER PUBLICATIONS

Japan Patent Office, Notice of Reasons for Rejection for application No. 2018-516188, dated Jul. 9, 2019 (2 pages + 2-page translation).

* cited by examiner

LINKED MICROMECHANICAL POSITIONING APPARATUS FOR REAL-TIME TESTING AND MEASUREMENT

PRIORITY

This application is a U.S. national application of the international application number PCT/FI2015/050689 filed on 13 Oct. 2015 the contents of which is incorporated herein by reference.

BACKGROUND

Applications involving measuring and controlling electrical and optical signals from micro- and nanometer scale targets are becoming increasingly common. This may involve the use of delicate probes with tip sizes starting from tens of nanometers, which may be positioned relative to the sample in multiple directions with nano- and micrometer scale resolution to accurately reach the target. Current technology makes it difficult or impossible to implement test arrangements that require fast control of probe position relative to the target or to implement test arrangements that involve many simultaneous tests or combinations thereof.

There is, therefore, a need for micromechanical positioning devices, which enable improved control of measurement probes.

SUMMARY

Now there has been invented an improved technical equipment by which the above problems are alleviated. Various aspects of the invention include an apparatus, a system, a method and a computer program product, which are characterized by what is stated in the independent claims. Various embodiments of the invention are disclosed in the dependent claims.

The present application relates to a device for positioning a measurement, manipulation and/or stimulation probe or another object relative to the target in a micromechanical fashion, performing measurements and tests, and/or stimulating or manipulating the target. The device may be a positioning device that is arranged to receive steering signals from other devices such as other positioning devices, other devices that measure, stimulate or manipulate the target, and/or steering devices like knobs, sliders or joystick controllers. The steering signals are decoded and interpreted by the positioning device and the positioning (the actuator(s)) are controlled based on the steering signals such that movement is effected based on the steering signal. As an example operation, another positioning device may transmit its movement information as a steering signal to the positioning device, and the positioning device may thus be able to move in synchrony with the other positioning device. The steering signal may be transmitted over a local network, e.g. over low-latency switched IP network. The device may be an integrated device such that electronics for measurement and/or controlling the micromechanical positioning are embodied in a physically contiguous unit, for example embodied inside a chassis. The application also relates to micromechanical positioning and measurement device capable of doing measurements, e.g. electrical and/or optical measurements, and/or stimulation and manipulation and/or various combinations thereof and that is capable of controlling probe position based on the measured information and, if applicable, capable of acquiring, processing, saving and/or transmitting such information in digital format.

The positioning apparatus may receive instructions for carrying out positioning based on the steering signals from an external control unit such as a computer. That is, instructions such as script code, computer executable (e.g. binary) code and/or parameters may be received from an external source such as a control unit to the positioning controller so that the positioning controller follows the positioning logic received at least partly from a source external to the positioning controller. This receiving may happen in the set-up phase of the testing or during the testing to provide adaptability to changing conditions.

There is provided a micromechanical positioning device, comprising a micromechanical positioning actuator for causing movement of a probe with respect to a target, a positioning controller, said positioning controller having an output, said output coupled to said actuator for controlling said movement, said positioning controller having a steering input, said steering input arranged to be coupled to at least one other device over a local communication connection to receive one or more steering signals from said other device, and said positioning controller arranged to control said movement based on said steering signals.

The positioning device may comprise memory for storing positioning control instructions, said positioning control instructions comprising computer-readable instructions suitable for use by said positioning controller in controlling said movement based on said steering signals, said positioning controller being arranged to control said movement based on said steering signals and said positioning control instructions. The positioning control instructions may comprise computer-readable instructions suitable for use by said positioning controller in controlling said movement based on sensor signals, said positioning controller being arranged to control said movement based on said steering signals, said sensor signals and said positioning control instructions. The positioning device may comprise an instruction input for receiving said positioning control instructions to said memory from a source external to said measurement device. The positioning device may comprise a sensor input for said positioning controller, said sensor input coupled to a sensor for receiving a sensor signal from said sensor to said positioning controller, said positioning controller arranged to control said movement based on said sensor signal in addition to said steering signals, and sensor read-out electronics for producing said sensor signal, said sensor read-out electronics being coupled to said sensor and to said sensor input of said positioning controller. The local communication connection may comprise a local communication network for carrying communication messages, and said steering input may comprise a communications controller operatively connectable to said communication network. The local communication network may be arranged to operate on a multicast or broadcast principle, and said positioning device may be arranged to listen to multicast or broadcast messages to receive said steering signals. The positioning device may be arranged to filter messages and control said movement based on such messages that are determined to be relevant to said positioning device. The communication messages may be messages packaged as communication packets for Internet Protocol (IP) transmission, said communication packets carrying at least one address and at least one said steering signal, said at least one address identifying at least one positioning device intended to receive said at least one steering signal. The positioning device may comprise a steering controller configured to form steering signals for other devices, and a transmitter configured to transmit said formed steering signals to other devices over said local communication connection. The steering controller may be configured to form a Quality of Service indicator for said steering signals for indicating the priority of said steering signals, said Quality of Service indicator being usable by a communications switch for prioritizing communication messages. The positioning device may comprise a steering controller configured to decode synchronization steering signals wherein said synchronization steering signals comprise information on movement of another positioning device, said steering controller configured to control said movement in synchrony with said another positioning device according to said synchronization steering signals. The positioning device may comprise a plurality of sensors, at least one micromanipulator actuator for causing movement of at least one sensor with respect to a target, said positioning controller having a plurality of sensor inputs, said sensor inputs coupled to said sensors for receiving sensor signals from said sensors to said positioning controller, and said positioning controller arranged to control said movement based on said sensor signals and said steering signals. The positioning device may comprise a steering controller configured to decode sensor steering signals wherein said sensor steering signals comprise information on a sensor reading of another device, said steering controller configured to control said movement according to said sensor steering signals.

There is provided a control unit for controlling a measurement and positioning system, comprising an interface for receiving user input from a user for controlling a measurement, a processor and a memory, computer program code in said memory, said code arranged to, when executed on said processor, cause said control unit to determine positioning control instructions based on said received user input, said positioning control instructions comprising computer-readable instructions suitable for use by a positioning controller of a measurement device in controlling movement of a micromechanical positioning actuator based on steering signals, and an instruction interface for providing said positioning control instructions to at least one positioning device of said measurement and positioning system.

There is provided a measurement and positioning system comprising a plurality of devices as described above and a control unit as described above coupled to one or more of said plurality of devices for providing positioning control instructions to said one or more of said plurality of devices.

There is provided a method for controlling a measurement device, comprising receiving steering signals from a steering input of said measurement device to a positioning controller of said measurement device, based on said steering signals, controlling a movement of a micromechanical positioning actuator causing movement of a probe with respect to a target.

The method may comprise receiving positioning control instructions from a source external to said measurement device, said positioning control instructions comprising computer-readable instructions suitable for use by said positioning controller in controlling said movement based on said steering signals, storing said positioning control instructions in a memory and controlling said movement based on said steering signals and said positioning control instructions.

There is provided a computer program product embodied on a non-transitory computer-readable medium, said computer program product comprising positioning control instructions that, when operated on by a processor, cause a micromechanical positioning device to receive steering signals from a steering input of said measurement device to a positioning controller of said measurement device, and based on said steering signals, control a movement of a micromechanical positioning actuator causing movement of a probe with respect to a target.

There is provided a computer program product embodied on a non-transitory computer-readable medium, said computer program product comprising computer code that, when operated on by a processor, cause a control unit of a measurement and positioning system to receive user input from a user for controlling a measurement, determine positioning control instructions based on said received user input, said positioning control instructions comprising computer-readable instructions suitable for use by a positioning controller of a measurement device in controlling movement of a micromechanical positioning actuator based on steering signals, and provide said positioning control instructions to at least one positioning device of said measurement and positioning system.

DESCRIPTION OF THE DRAWINGS

In the following, various embodiments of the invention will be described in more detail with reference to the appended drawings, in which.

DESCRIPTION OF EXAMPLE EMBODIMENTS

Figure 1A:
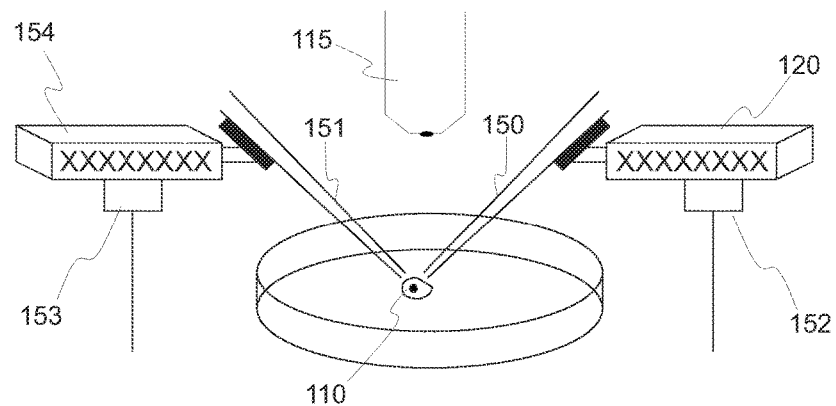
FIGS. 1a and 1b show an example of positioning a probe and carrying out electrical measurement from cell in micromechanical manner.

In the following, several embodiments of the invention will be described in the context of micromechanical manipulation. It is to be noted, however, that the invention is not limited to the presented examples. In fact, the different embodiments may have applications in any environment where accurate and fast positioning of measurement sensors is required.

The invention may in the following be also described in the context of electrical and/or optical measurements that are performed using sensor(s) that are positioned related to the target(s) in micromechanical fashion, where test arrangement involves simultaneously implementing many tests or using measured information to control test in closed-loop manner. It is to be noted, however, that the invention is not limited to examples described here. In fact, the different examples may have applications widely in any environment, where precise positioning of any kind is needed. For example, arrangements in optics, materials testing and other areas may benefit from the use of linked positioning devices.

A positioning device as disclosed may receive steering signals from another device, such as another positioning device, a sensor device or a steering device. The steering signals are received over a local communication connection such as an Ethernet connection with a speed of 10 Mbit/s, 100 Mbit/s, 1000 Mbit/s or another speed. The steering signals may comprise messages, such as a short data structure comprising information on a step of movement of another device.

Positioning in the range of nanometers, tens or hundreds of nanometers, micrometers and tens or hundreds of micrometers, or in the range of millimeters may be understood to be micromechanical positioning. It is also often necessary to simultaneously perform many measurements or tests, which involves simultaneous use of a plurality of probes, positioning units and electrical and/or optical measurement or stimulation units. It is also typical that tests need to be automated, which may mean that probes need to be moved relative to the target automatically, for example in a scanning fashion covering a certain space or surface, or to go through certain measurement targets in a sequence (like microcircuits). The measurements and/or stimulation may also be automatically controlled, that is, the test sequence or sequence of measurements may be automatically carried out according to instructions (logic and/or parameters) received from a control unit.

The disclosed positioning device may be used in electrical measurements of biological signals from living cells while controlling their properties through electrical and/or optical stimulation. This may involve use of sensor probes with tip sizes starting from tens of nanometers, which may be positioned relative to the sample in multiple directions with nano- or micrometer scale resolution to accurately reach target. After reaching the target, the probes may be able to stay in the same position during the measurements and thus mechanical vibrations or drifting of the position may not cause problems. In addition to biological measurements there are also many similar applications in technical fields such as probe stations in failure analysis.

Further on, because small samples may be monitored with special equipment such as microscopes with special environmental control chambers, there often is very limited space available to implement all required instrumentation. Small size of a measurement device may also enable close-up installation, which enables using short probes and thus minimizes mechanical lever arms for environmental or user induced vibrations, and minimizes thermal drifts in position. As disclosed here, implementing complex tests and measurements efficiently may benefit from integrating all the instrumentation physically and/or electronically in such a way that information gathered and processed during the tests is available for real-time automated control and data is also saved synchronously in digital format to a memory.

It has been noticed in the present invention that earlier solutions for performing tests and measurements involving multiple electrical and/or optical measurements from micro- and nanometer scale targets using probes that are positioned in micromechanical fashion do not fulfil these needs completely. Currently such test systems are implemented using separate electrical and/or optical measurement apparatuses, which are connected to their separate control boxes, which then connect to a separate data acquisition system. The data acquisition system is in turn then typically connected to computer, which further on connects to separate positioning apparatus control box, which finally sends command to positioning apparatus to move probe based on measured information. Such complex systems are difficult and expensive to build and operating them requires special skills. It has been noticed here that the performance of earlier systems for positioning is not satisfactory because of the associated delays between separate apparatuses, which are typically connected to each other, for example, through slow serial communication interfaces. It has been noticed here that another disadvantage is that such systems become too large in size to fit inside limited space available in the test environment. Therefore, it may not be physically possible, for example, to implement simultaneous measurements with many probes. It has been noticed here that the large size of the system also means long mechanical lever arms in the system, which reduces mechanical stability and exposes the system to thermal drifts. It has also been noticed that the earlier solutions seem to be prone to high noise and thus low quality of measured information.

Figure 1B:
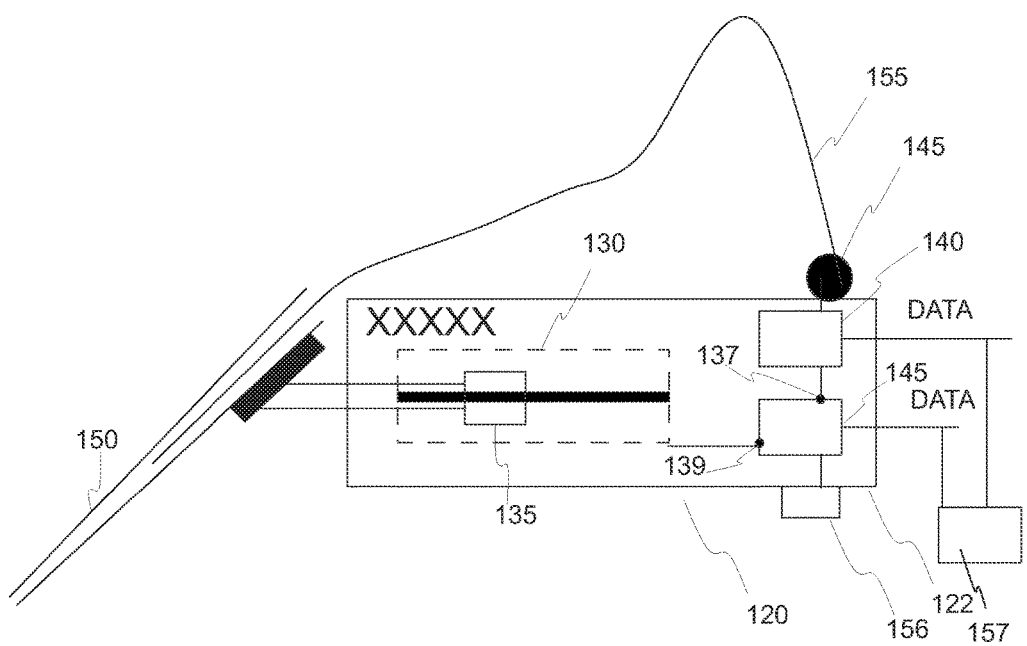

FIGS. 1a and 1b show an example of a positioning devices 120 (154) which comprise a micromechanical positioning actuators 130 for causing movement of a probe 150 (151) with respect to a target 110 in a micromechanical manner. A positioning controller 145 is coupled to the actuator 130 for controlling the movement of the probe 150 (151). The positioning controller 145 has an output which is coupled to the actuator 130 through an interface or connection 139 for controlling the movement of the probe 150. The positioning controller 145 is connected to a steering input 156 for receiving a steering signal from a source external to the positioning device. For example, another positioning device or a sensor device or a steering device may provide this steering signal. A control unit 157 may provide instructions for decoding and using this steering signal to control the positioning. For example, two positioning devices may be sending steering signals to each other, informing each other on their position and/or speed and/or acceleration, and they may in this way move in synchrony. In a similar manner, a number of sensor and positioning devices may be connected over a local communication connection and they may operate as a group by sending steering messages to each other.

The steering signals may comprise positioning commands, positioning information or parameters of various kinds, and/or measurement data. The steering signals may, for example, be movement commands to move a certain distance or to move with a certain speed to certain direction, and they may be generated by a positioning device or a steering device such as a joystick controller. The steering signals may be short data structures, for example of the order of 10-100 bytes, or even hundreds of bytes or even more. The individual steering signals may be short in transmission duration, for example so that the individual steering signal may be sent in a time of a few microseconds, or even less, which provides for low latencies in the control of the positioning. For example, with a 1000 Mbit/s transmission speed, a 50-byte steering signal may be sent in less than a microsecond. As another example, a 100-byte steering signal sent over a 10 Mbit/s connection may take a duration of approximately a microsecond. This may be less than what can be usually achieved with state of the art systems for nano- and micropositioning. IP protocol network may add some delay due to packet processing, but this delay is also less than the processing delay by a conventional control unit.

A device may have a capability to both receive and send steering instructions. Some devices may have the capability to receive, modify and forward the processed steering instructions, thereby adding as steering signal transcoders.

The positioning controller 145 may in addition have an input which is coupled to the sensor 150 for receiving a sensor signal from the sensor to the positioning controller 145. The positioning controller 145 may be arranged to control the movement of the sensor 150 based on the sensor signal. The measurement device 120, i.e. a positioning apparatus, may move the sensor 150, and the target 110 may be observed e.g. using microscope 115. The measurement device 120 may comprise read-out electronics 140 for producing a sensor signal. The read-out electronics 140 may be connected to the measurement sensor 150 through an interface 145 and an electrical lead and to the input of the positioning controller 140 through an interface 137.

The read-out electronics 140 may be capable to measure analogue or digital electrical signals and send measured signal digitally to external computer 157, or to microcontroller (not shown) or processor (not shown) that is located in the measurement device 120. Alternatively, the electrical signal may be converted to be suitable for transferring in analogue format to measurement device 120 for AD conversion before transmitting to the microcontroller or processor. The measurement device 120 may comprise the positioning controller 145 to electronically control the sensor position with micro- to nanometer resolution (or less or more accurately) using electronically controlled actuator 130, which may comprise motors such as stepper motors, servo motors or piezo motors. This control may be done automatically based on the steering signals and instructions for using the steering signals. The positioning control instructions in the form of executable computer code, script code and/or parameters may be received from an external control unit or computer 157, which is connected to the apparatus for example using Ethernet. The positioning controller may then follow the positioning logic received at least partly from a source external to the positioning controller (some of the control logic and parameters may already exist on the device). This receiving may happen in the set-up phase of the testing or during the testing to provide adaptability to changing conditions. The measurement device 120 may include means to save and process data and/or transmit it forward to controller or computer or internet.

The measurement device 120 may comprise an enclosure, body or another contiguous structure 122. The positioning controller 145 and the read-out electronics may be embodied within this continuous structure. For example, the different components may be built on the same circuit board or microcircuit. The actuator 130 may be built as part of the continuous structure, or partly outside it, or completely outside.

The sensor 150 may be an electrical sensor arranged to detect a voltage and/or current at the sensor. The sensor read-out electronics 140 may comprise an amplifier for amplifying the detected voltage and/or current. A sensor may also comprise capability of measuring capacitance or conductance by employing a bias signal (DC bias for conductance/resistance and AC bias for capacitance). A contact to a metal or semiconductor surface may be detected by resistance measurement without the need of an amplifier by using a signal level detector. In a similar manner, liquid level where biological sample is embedded in may be detected. This detection may be used in controlling the positioning. Alternatively or in addition, the measurement device 120 may comprise a sensor for measuring bioelectric signals, for example a patch-clamp sensor, or a force sensor, or a sensor for sensing chemical environment, for example pH level.

Alternatively or in addition, the sensor 150 may be an optical sensor, and the sensor read-out electronics 140 may comprise an optical-to-electric converter coupled to the optical sensor and to the input of the positioning controller 145. The optical sensor and the read-out electronics may be arranged to detect intensity, wavelength (spectrum), polarization or any other property of light (electromagnetic radiation in general). The measurement device 120 may comprise an image processor, where the image processor may perform pattern recognition and/or other image processing tasks and produce a signal to the positioning controller. The optical sensor may also be embodied on the same circuit with the positioning controller. For example, in cases when the bandwidth of the electronic communication bus between the read-out electronics and the positioning controller would be a bottleneck, a direct optical fibre connection of light to be measured to the controller may alleviate this problem.

An individual sensor 150 may be positioned first manually using electronic positioning controller 145 by observing the target 110 and sensor 150 with increasingly large magnifications when approaching the target 110. Electrical signal may be measured during the positioning and a final approach may be done manually or automatically based on the characteristics of the measured signals such as change in the voltage level or sensor impedance as defined in the positioning control instructions. When a good contact between the sensor 150 and test target 110 is achieved many automated measurements may be made while stimulating the test target 110 electrically for example measuring voltage while injecting current pulses or controlling voltage with pulse protocols and measuring currents. Good test condition may be maintained by fine tuning the sensor position based on monitored electrical characteristics for example if the target 110 is slightly moving or deforming, which may happen for example when doing tests with living cells or samples.

The measurement device may have integrated means to measure electrical and/or optical signals and use information from those signals for closed-loop positioning. It may also acquire and process and/or save and/or transfer measured data forward that includes electrical and/or signal and positioning information, i.e. relative timing of different information may be acquired with high precision and provided as part of the measurement data and provided over a computer interface e.g. to a control unit.

The measurement and positioning devices may be able to acquire multiple different measurement signals in parallel, e.g. resistance and capacitance against probes or against target substrate or combination of them. As well as measuring many signals of the same modality simultaneously using many sensors/channels, parallel measurements of different modalities may also be done.

Electronically controlled measurement device may comprise one or more degrees of freedom of movement that can be linear or rotation or whatever kind of movement.

The actuator 130 may comprise one or more moving elements 135. The moving elements may be arranged to be moving e.g. by a piezoelectric drive, or by employing a stepper motor, or any other type of drive that is suitable for micromechanical positioning. Such actuators suitable for micromechanical positioning may be integrated or functionally connected to other equipment. For example, the actuator may be connected to a microscope or may be part of a microscope.

The actuator 130 may have high precision capability for the micromechanical positioning, for example positioning resolution may be few nanometers or even less than nanometer or few tens of nanometers, and repeatability of the positioning may be few nanometers, few tens or hundreds of nanometers or between micrometer and few tens of micrometers. Such high precision positioning applications may require inaccuracies and drift in the position over time to be less than few hundred of nanometers per hour or even less or less than few micrometers. The optical/electrical measurement units 140 may have high precision, for example voltage measurement resolution may be few microvolts or even in nanovolt range or in the range of millivolts and current measurement resolution few picoamperes or even in femtoampere range or in the range or nano and milliamperes. Noise in the high precision electrical measurements may be small and may not exceed microvolts or even less or few hundred of microvolts, or less than few or few hundred of picoamperes or even less than a picoampere. For high precision optical measurements resolution may need to be at the single photon level and noise may need to be also in this magnitude, or the resolution and noise requirement may be few tens, hundreds, thousands or even larger number of photons from very short time periods to seconds. The stimulation precision requirements may be at the similar level as the measurement and positioning requirements. The positioning controller 145 may be able to operate with low latency and high synchrony with the measurement unit 140, for example latency may be few microseconds or even less, few tens or hundreds of microseconds or few milliseconds in comparison to conventional solutions where latencies are typically few tens of milliseconds or more.

Figure 2:
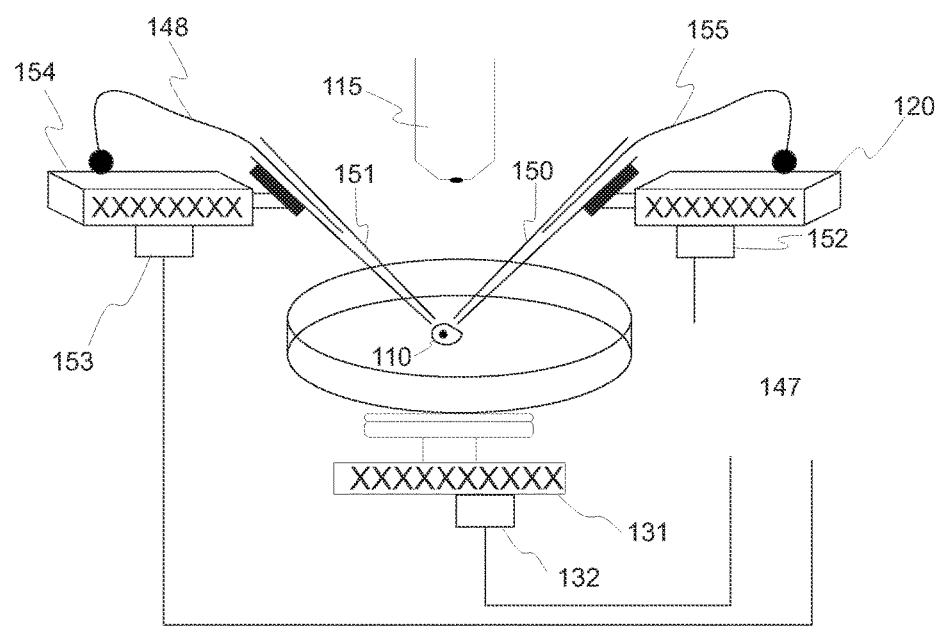
FIG. 2 shows an example of a measurement arrangement where the sensor is held stationary and the target is moved in micromechanical fashion.

FIG. 2 shows an example of a measurement arrangement where the sensor 150 is held stationary and the target 110 is moved in micromechanical fashion. The positioning device 131 may move the sensor or the target in multiple directions. For example, the sensor may be stationary, i.e. not moving, and the target may be moved. The movement may be measured and controlled based on the measurement. The target may be on a petri dish or some other suitable bed settled on a sample holder. The target may be mechanically coupled with the actuator. For example, the target may lie on top of the actuator, or it may be mechanically connected to the actuator, for example with the help of a sample holder. For example, a sample holder may be screwed or glued to the actuator, and the sample holder may have means for holding the target. The actuator and/or the micromechanical positioning device 131 may be connected to or may be part of a microscope table, a sample holder or other equipment.

The complete micromechanical positioning device may also be arranged to move with respect to a target. For example, the device may be installed on tracks or wheels or other means to move the positioning device. For example, the device may be arranged to move on top of a surface to be measured or tested, such as on top of biological tissue, or on top of a materials surface to be tested.

The positioning device may also comprise a plurality of actuators that are arranged to move with respect to the target and with respect to each other. That is, both the sensor(s) and the sample may be arranged to be movable with respect to each other. For example, as shown in FIG. 2, there may be a plurality of positioning devices 120, 131, 154, each having a respective steering input 152, 132, 153. The steering inputs may be connected to a local network 147, and they may be able to act as outputs of steering messages from the respective positioning devices. Some or all of the positioning devices may have probes 150, 151 and sensors 148, 155 coupled to them, as explained earlier.

Figure 3A:
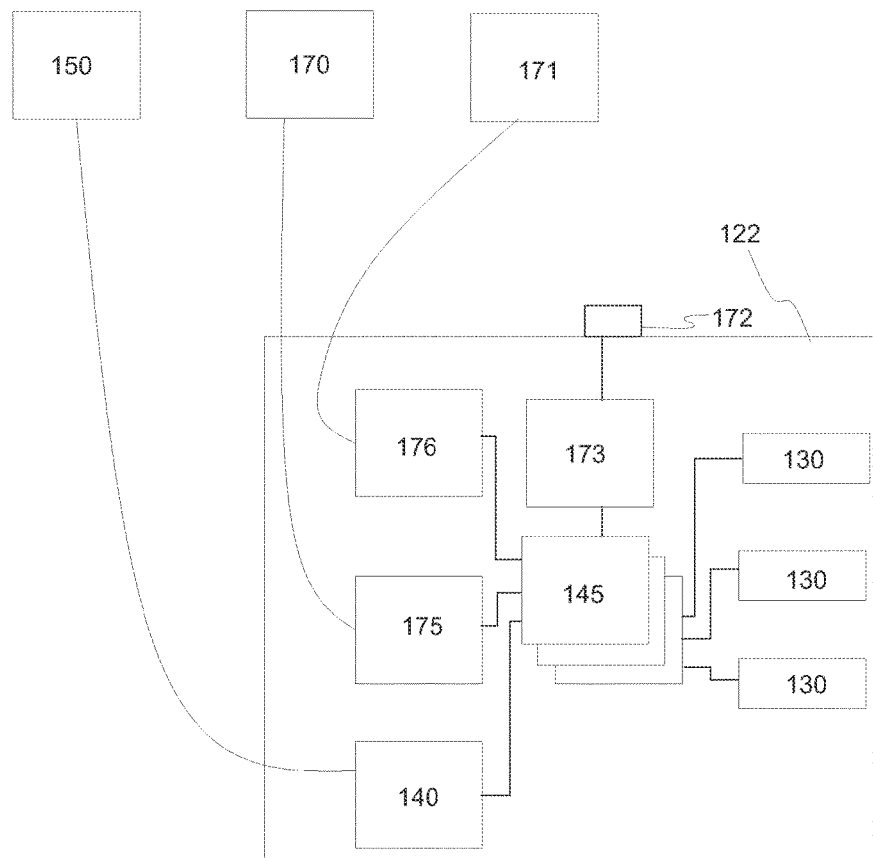
FIGS. 3a and 3b show example schematic representations of a positioning apparatus with capability for receiving and sending steering signals.

FIG. 3a shows an example schematic representation of connections of an integrated positioning apparatus with steering signal input and/or output. As described earlier, the positioning apparatus may have a steering signal input 173 coupled to a communications port 172 and the one or more positioning controllers 145. This enables the positioning apparatus to receive steering signals, as explained earlier, and to control the positioning based on the received steering signals. For example, the steering signals may comprise position, speed and/or acceleration information of one or more positioning devices. The steering signals may comprise sensor information such as voltage, current, capacitance, resistance, pH, temperature, humidity, pressure or other such information. The steering signals may comprise force information (e.g. from probes attached to positioning devices), information extracted from imaging by video or image analysis, feature detection, object size or colour or number information. The positioning controller(s) 145 may comprise logic built-in and/or received as instructions to interpret the steering signals and to convert the steering signals to a control signal to the actuators 130.

The positioning device may also have electrical and/or optical measurement and/or stimulation capabilities. The apparatus may comprise or be connected to various sensors 150, 170, 171, as presented earlier. Various types of probes/ sensors may be attached to the apparatus that are suitable of doing various type of electrical and/or optical measurements, such as microelectrodes or probes; electrical measurement may include means to compensate for the electrical characteristics of the probe and target, such as compensate for the probe capacitance or some optical characteristics of the optical measurement probe or target.

The sensors may be connected to their respective sensor read-out electronics 140, 175 and 176 as described earlier, or the read-out electronics may be a single unit receiving a plurality of sensor inputs. For example, the sensor read-out electronics may comprise integrated chip amplifiers for recording signals from living cells with one or more channels. The read-out electronics may also comprise a stimulator or current-supply element for providing voltage, current and/or light to the target being measured. That is, in addition to electrical measurement it may also be possible to control electrical characteristics of the target, i.e. control its voltage and/or inject current while doing electrical measurements. Also, in addition to optical measurement it may also be possible to stimulate target optically and combine this stimulation with electrical and/or optical measurements or any other type of measurements to measure the stimulation response. In an analogous manner to electrical stimulation, injection of current may also be used to program permanent fuses on semiconductor circuits (setting bits to 0/1 on the chip).

The positioning apparatus may comprise integrated means of measuring electrical and/or optical signals, comprising measuring voltage and current or doing optical measurements such as intensity or wavelength. Integration may be understood as the measurement being directly connected to the positioning controller (controller for the micromechanical actuator(s)) that is integrated in the apparatus. The positioning controller may be arranged to receive instructions from an external control unit such that these instructions are used in the controlling of the positioning as the logic or parameters for the measured sensor input.

The output of the read-out unit(s) may also be connected to the manipulator positioning controller(s) 145 for controlling the positioning, e.g. doing closed loop positioning based on measured signals. Both the read-out electronics and the controller may provide their data out through a data output so that they can be saved, that is measured signals and positioning signals may be provided. Information from the measured signals in one manipulator may be also be used to control other manipulators for synchronous positioning.

For example, in a microelectronic probing application example instructions 300 may be to "approach target whose coordinates are known with some accuracy by moving the probe in a scanning fashion until resistance measured electrically in real time reduces below certain threshold that signals physical contact and then stop moving". For example accuracy of coordinates may be from few micrometers to few tens and hundreds of micrometers and positioning resolution during scanning may be in range from few nanometers to few tens and hundreds of nanometers. Real time may for example mean delays in the closed loop control that is few tens or few hundreds of microseconds. Another version is to "measure in parallel the capacitance when approaching the target, reduce speed when the capacitance increases (the capacitance increases when close to target) and stop when a predetermined reduction in resistivity is detected". The small delays achieved by this closed loop test control may enable faster probing and may prevent crashing the probe to target.

Another example for instructions 300 in biological tests may be automated patch clamp experiments, such as "load a micropipette (with electrically conducting solution) with positive pressure to help keeping tip clean when moving in tissue, then drive pipette forward in tissue while measuring electrical impedance, stop when impedance increases above a given threshold (signals that pipette tip is touching cell membrane), change to small negative pressure in pipette to stabilize contact forming, start measurement".

Another version of instructions 300 could include a rule for measuring impedance intermittently during measurements and correcting pipette tip position if impedance changes. For these applications, there may be an integrated pressure control in the measurement device. Positioning resolution required in implementing this type of instruction may for example be in the range from few nanometers to few tens and hundreds of nanometers or even less than nanometer when correcting the pipette tip position during the measurement, and delays in the closed loop control may need to be from few tens or few hundreds of microseconds.

Another example of instructions 300 for optogenetics experiments may be as follows: "move optical fiber forward in the brain tissue to approach target area known with certain accuracy, simultaneously measuring fluorescence signal while moving forward and stop when signal exceeds given value". A version of instructions 300 could include a rule for adjusting fiber position slightly if measured fluorescence signal base-line changes in certain manner.

The positioning device may be integrated in a contiguous structure 122. This may provide the advantage of electrical shielding. Furthermore, as the measuring and position control are closely integrated, delays may be avoided, thus enabling more accurate and faster positioning. Also, the size of the device may thereby be small enough e.g. to fit under a microscope lens and/or to enable access to the sample from almost horizontal direction.

Figure 3B:
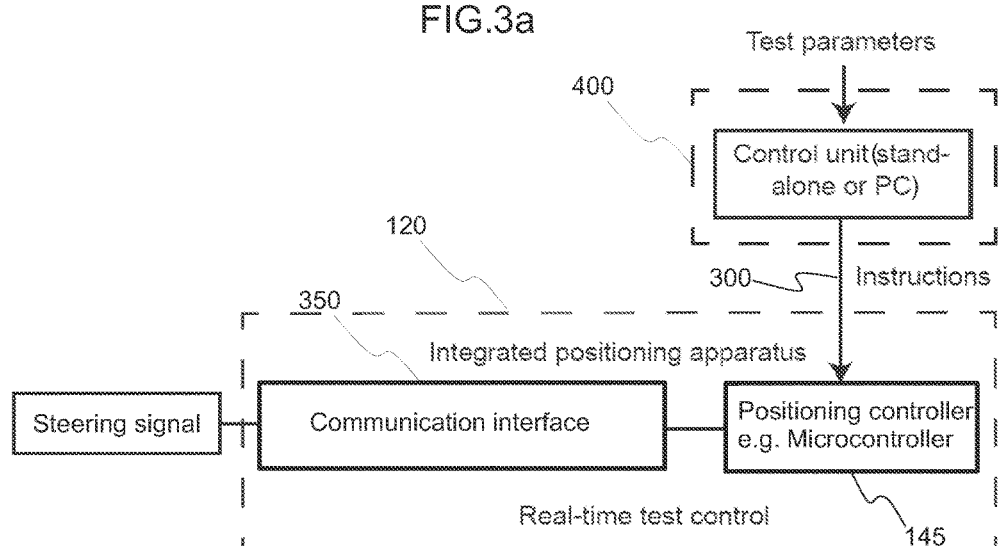

FIG. 3b illustrates the functional units of an exemplary measurement and positioning system.

The measurement and positioning device may have integrated means to receive steering signals from a steering input 172 with the help of a communication interface 350 and to use information from those signals for integrated real-time test control based on instructions from external control unit 400. That is, an external control unit 400 does not need to perform closed loop test control or to act as a central real-time controller or intermediate processor. Instead, the control unit 400 may provide instructions 300 to positioning controller 145 of integrated positioning apparatus 120 on what to do with the received steering information. The instructions 300 can vary a great deal e.g. from individual parameters to a set of parameters and/or script language instructions or executable computer code, or any combination of these.

The device may have an instruction input for receiving positioning control instructions to a memory from a source external to the measurement device, such as a control unit. The positioning device may have memory for storing the positioning control instructions, and these are later arranged to be used to control the actuator movement based on the steering signals. For example, the positioning controller may be a microcontroller-based element, and the control unit 400 may provide code and parameters as instructions 300 to the microcontroller. The measurement and positioning system 120 may be at least partly embodied in a casing 122. The communication interface may provide a connection to conventional LAN technology, such as twisted-pair Ethernet network. Alternatively, the communication interface may be simplified so that the interface does not use line transformers/drivers, but instead these exist only at the side of the network hub or switch. The communication interface 350 may also provide connection to a wireless LAN segment. As an example, the instructions 300 may also be received through a communications connection provided by the interface 350.

The positioning device may be arranged to filter incoming messages and control the movement based on such messages that are determined to be relevant to said positioning device. For example, the steering messages may have an address or they may have a type carried on the message, e.g. in a message header.

The positioning device, or a sensor device, or a steering device may also be arranged to transmit steering signals. The communication interface 350 or another interface may encapsulate the signals from the positioning controller (such as position, speed, acceleration or sensor readings) to a format of the steering signals suitable for transmission and provide the steering signals over a communication connection to other devices.

The steering controller may be configured to form a Quality of Service indicators for the steering signals for indicating the priority of the steering signals. Such Quality of Service indicators may be usable by a communications switch for prioritizing communication messages. This helps to enable low-latency communication for the steering messages, while other messages on the network, such as measurement data, may have a low priority.

Figure 4:
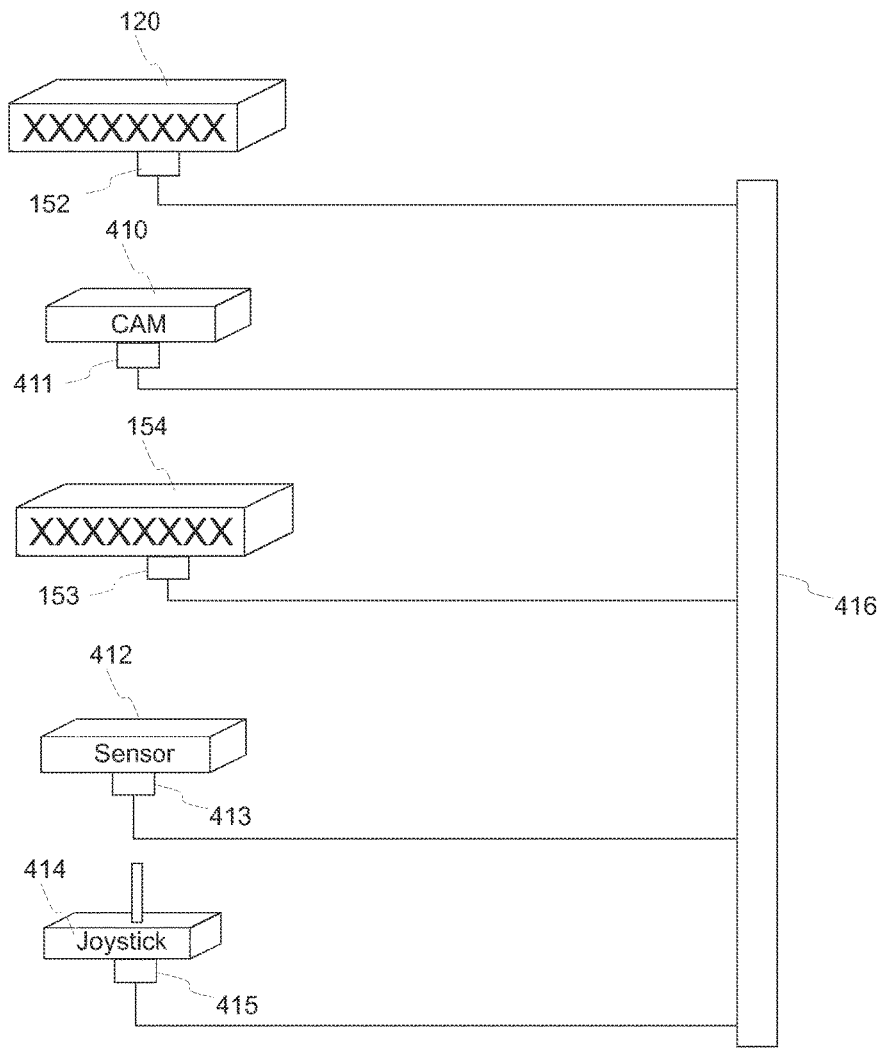
FIG. 4 shows a system of linked devices sending steering signals between devices.

FIG. 4 shows a system of linked devices sending steering signals between devices. There may be positioning devices 120, 154, camera or image analysis devices 410, various sensors 412 and steering devices 414 like a joystick. The different devices are connected via their steering signal input/output 152, 153, 411, 413, 415 to a local communication network formed by one or more network nodes like hubs and/or switches 416. The different devices may be physically arranged to e.g. be in touch with or in close proximity to a sample being analyzed. For example, the devices may be arranged around a microscope.

The communication messages carried in the local network may be messages packaged as communication packets for Internet Protocol (IP) transmission. The communication packets may carry one or more addresses and at least one steering signal, where the address(es) identify at least one positioning device intended to receive the at least one steering signal.

The network may be arranged to be a real-time network, and the communication packets may not be routed outside the network. The network may be e.g. a full-duplex twisted-pair Ethernet network with a speed of 10 Mbit/s, 100 Mbit/s, 1000 Mbit/s or more. The network layer may employ IPv4 addressing or IPv6 addressing, or another addressing scheme. TCP protocol may or may not be employed, or UDP protocol may or may not be employed.

Also, a proprietary transmission control protocol may be used. A control unit may not be involved in routing the messages, and thus application layer operational delays may be avoided, as switches and other network nodes typically employ hardware-based handling of messages. On the other hand, a control unit may physically include a switch or hub 416 for creating the local network.

A sender may send the same steering message to multiple recipients, specified by an address or message type, for example. The messages may carry the sender and recipient identifiers, and a message identifier (packet order). The messages may carry an acknowledgement request. Multicast and broadcast messages may be used to reduce the number of transmissions and thus increasing bandwidth. Binary packets over UDP/IP may be used to save transmission time.

The positioning devices may be running a real-time operating system as an operating system.

Figure 5:
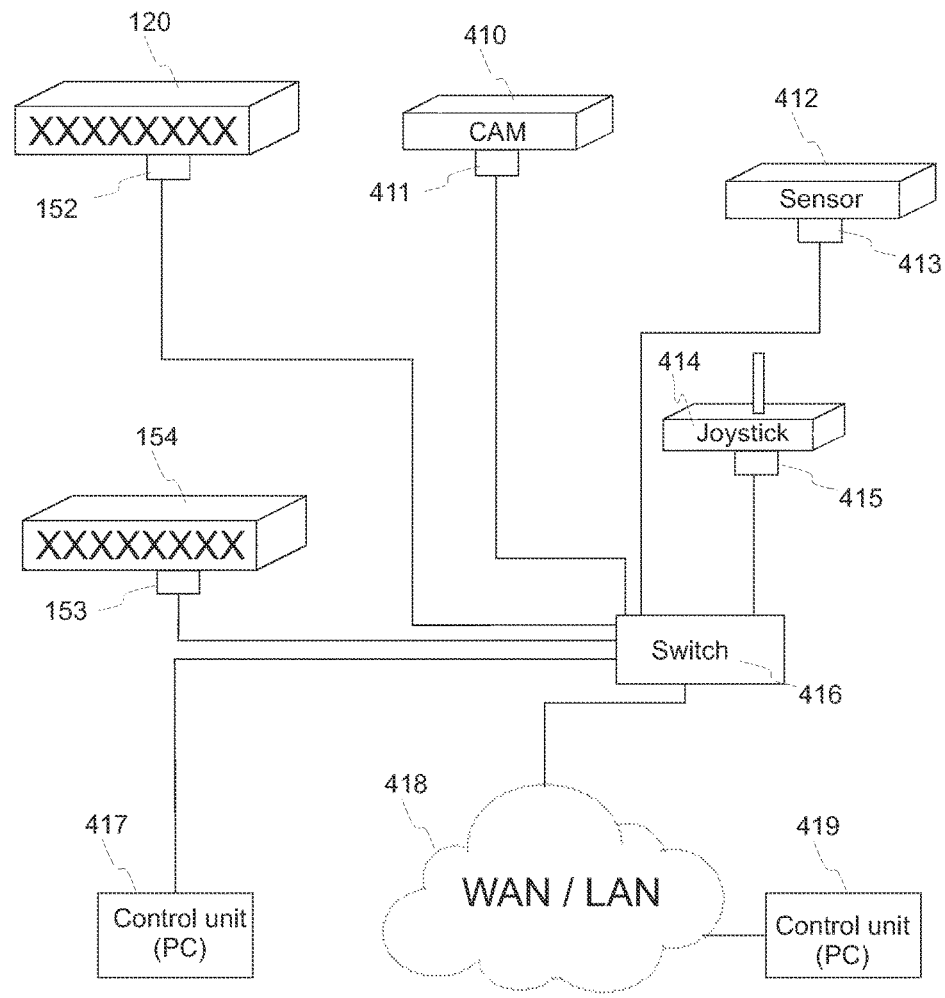
FIG. 5 shows a measurement and positioning system with a plurality of linked devices and a control unit.

FIG. 5. shows an example measurement and positioning system with a plurality of linked devices and a control unit. As shown in FIG. 4, the system may have a plurality of devices, and a network node such as a switch. There may also be one or more control units 417, 419 such as personal computers or special purpose control units. The local network may be connected to a wide area network WAN 418, for example for the purpose of being able to convey measurement data to an external memory (e.g. a control unit). In this context, the wide area network WAN 418 may be understood to be any other network or group of networks, for example a laboratory local area network, a group of local area networks, the internet, any dedicated (private) network and the like. The wide area network may be connected to the local network using a router for routing communication between the local network and the wide area network. Also, a firewall may be used to block unwanted traffic, for example with network address translation.

The control units may, through sending instructions to devices, may define for example such various matters like:
Source device of synchronous movement (set role to position transmitter), target devices for the same (set role to position listeners)
Positioning transformations, such as parameters for the trigonometric transformations when the positioning devices have different alignment around a target
Conditions for movement, such as start/stop conditions, ranges, triggered movement of a predetermined distance based on a steering message etc.
Direction of rotation, coordinate system etc.
Defining steering source to be a sensor, conditions and mapping of sensor values to different movements
Lock to image: keep the probe in place based on image analysis from an image analysis device
Trigger movement: when any device detects contact, it sends a steering command to others to stop or to move up a certain small distance (to avoid crashing to surface)
Follow table: all positioning devices follow the movement of the microscope table
Provide data: a device sends a start data steering command to other devices when it detects contact with the target, and other devices start sending measurement data (e.g. to be stored)

As an example application of FIG. 5 setup, a data sample stream not being time critical may be routed to an external network for further storage or analysis, or even to the internet, while time critical signals (steering signals) are processed inside the environment.

In the arrangement of FIG. 5, all devices on the system may be able to communicate with each other without using any intermediate router node. The devices may be connected to the switch or hub directly or capacitively, i.e., having no transformer or only one line transformer on the switch side. This enables making the devices more compact. Some other devices e.g. an electronic control unit with user interface may be connected to the same switch via its standard Ethernet port. The system may be extended with a wireless LAN segment, which may be bridged to the low latency LAN island or connected via a router (then the wireless segment not being part of the latency critical applications but e.g. providing a remote user interface).

Connecting the positioning devices over a low-latency local network may provide advantages. For example, USB to serial converters are often used in state of the art system as an interface between devices and the central control unit, which introduces delays and delay jitter. Overall such traditional systems involve various message buffering and transform instances as well as delays and delay jitters between the measured signals and control actions, which may now be avoided with the present system to have real time control and high synchrony level. Namely, it has been noticed here that significant amount of the delay and delay jitter is introduced by the centralized control processor (often a PC) running non-real time operating system, where task (thread/process) switching and thus also the trigger line interrupt handling (up to the application layer knowing how to handle it) may take tens of milliseconds. Such delays may also be avoided, as in the present system, the control unit may not take part in the real-time time-critical operations, but merely send instructions to the devices for handling the inter-device steering signals.

Figure 6A:
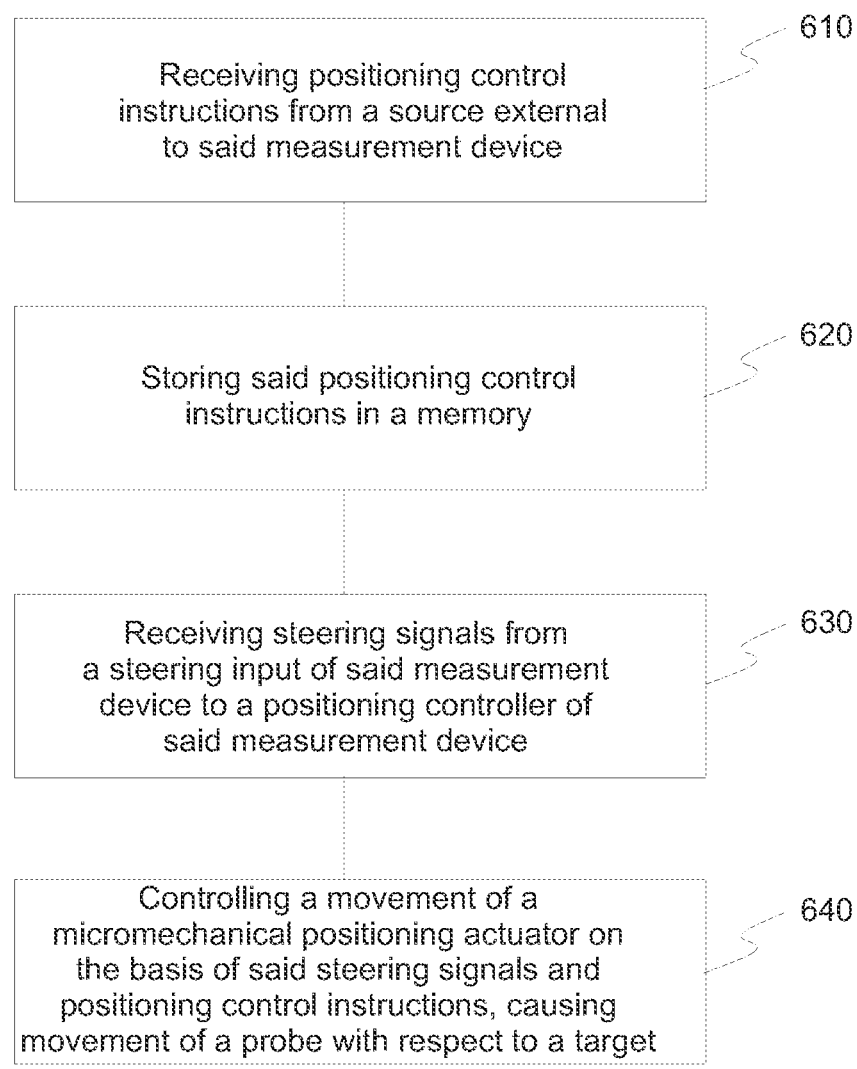
FIGS. 6a and 6b show example flow charts for controlling a measurement device.

FIG. 6a shows an example flow chart for a method for controlling a positioning device. In phase 610, positioning control instructions may be received from a source external to said measurement device, where the positioning control instructions comprise computer-readable instructions suitable for use by the positioning controller in controlling the actuator movement based on steering signals. In phase 620, the received positioning control instructions may be stored in a memory directly or after decoding and/or processing. In phase 630, steering signals may be received from a steering input of the measurement device to a positioning controller of the measurement device. Based on the received steering signals, movement of a micromechanical positioning actuator may be controlled, causing movement of a probe with respect to a target in phase 640.

Figure 6B:
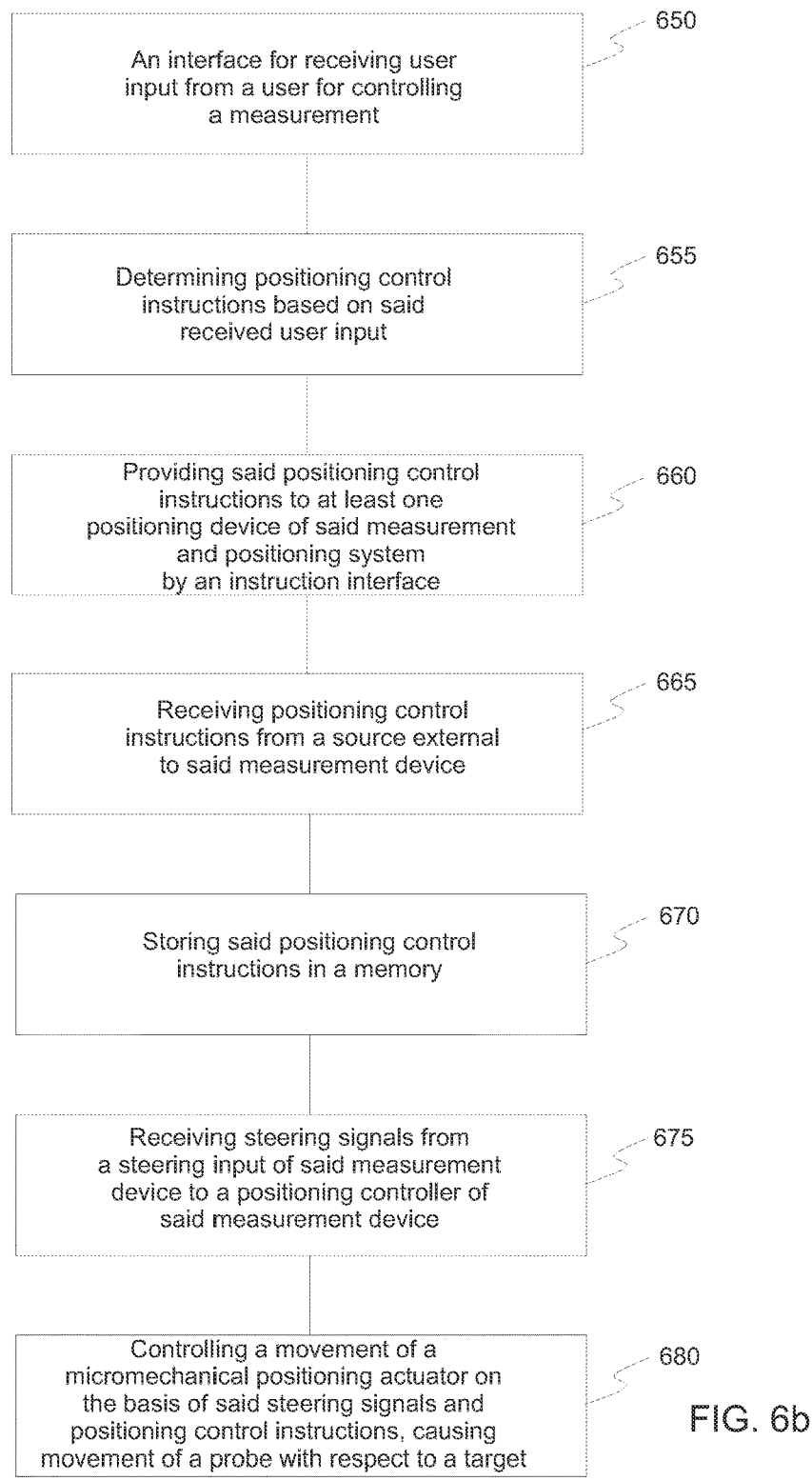

FIG. 6b shows an example flow chart for a method for controlling a positioning system. In phase 650, user input may be received to a control unit from an interface for controlling a measurement. In phase 655, control instructions may be formed based on the received user input. For example, computer program code or parameters may be formed into a control instructions message. In phase 660, the control instructions may be provided to at least one positioning device through an instruction interface. Different devices may receive similar instructions or they may each receive instructions specifically compiled for each device. In phase 665, positioning control instructions may be received from a source external to said measurement device, where the positioning control instructions comprise computer-readable instructions suitable for use by the positioning controller in controlling the actuator movement based on steering signals. In phase 670, the received positioning control instructions may be stored in a memory directly or after decoding and/or processing. In phase 675, steering signals may be received from a steering input of the measurement device to a positioning controller of the measurement device. Based on the received steering signals, movement of a micromechanical positioning actuator may be controlled, causing movement of a probe with respect to a target in phase 680.

The measurement device may receive instructions 300 from a control unit 400 for carrying out positioning control with the positioning controller 145. These instructions 300 may be formed as a computer program product embodied on a non-transitory computer-readable medium, where the computer program product comprises positioning control instructions that, when operated on by a processor, cause the measurement and micromechanical positioning device to receive a steering signal as an input to a positioning controller, control a movement of a micromechanical positioning actuator, causing movement of a sensor with respect to a target by using said positioning control instructions in determining said movement based on said steering signal.

The control unit 400 may have a computer program comprising computer code that, when operated on by a processor, cause a control unit of a measurement and positioning system to receive user input from a user for controlling a measurement, determine positioning control instructions 300 based on said received user input, said positioning control instructions 300 comprising computer-readable instructions suitable for use by a positioning controller of a measurement device in controlling movement of a micromechanical positioning actuator based on a steering signal, and provide said positioning control instructions to at least one measurement device of said measurement and positioning system.

The measurement and positioning devices described here may have various application areas. For example, the measurement device may be used in materials testing and fault analysis, production and quality control automation applications, measurements of electrical circuits, biomedical diagnostics and drug development measurements of living cells and any other areas where precise positioning of the measurement sensor is important and where position adjustments based on steering signals from other positioning devices, sensor devices and/or steering devices may be required with small latencies.

One application may be to control several positioning devices with high precision and low latency in a synchronized manner based on information from another device in the environment. Another applications may be to control positioning devices with high precision and low latency in a synchronized manner based on information measured by a sensor or another measurement apparatus connected to the environment, such as electrical biosignal measurement apparatus, force signal measurement apparatus or optical imaging apparatus.

In addition to controlling positioning, multi-channel measurement data sample streams from different apparatus connected to the environment may be carried via the same physical connections carrying also the latency critical steering signals.

The various embodiments of the invention can be implemented with the help of computer program code that resides in a memory and causes the relevant apparatuses to carry out the invention, or with circuitry achieving the same. For example, an integrated positioning apparatus may comprise circuitry and electronics for handling, receiving and transmitting data, computer program code in a memory, and a processor that, when running the computer program code, causes the positioning apparatus to carry out the features of an embodiment. Yet further, a computer may comprise circuitry and electronics for handling, receiving and transmitting data, computer program code in a memory, and a processor that, when running the computer program code, causes the computer to carry out the features of an embodiment.

The various embodiments of the invention can in addition be implemented with the help of an integrated measurement and positioning apparatus comprising the relevant characteristics to carry out the invention, or with devices achieving the same. For example, a mechanical precision instrument may comprise mechanical parts, electrical circuits or components and programmable elements or devices that, when operating the instrument, causes the devices to carry out the features of an embodiment.

The various embodiments of the invention can be further implemented with the help of an electronic circuit comprising the relevant apparatuses to carry out the invention, or with devices achieving the same. For example, an external control device connected via a command port or an interface may cause a positioning controller to carry out the features of an embodiment. Further, an electronic circuit may comprise tools for handling, receiving and transmitting data. The circuit may contain a processor and a program code in a memory, that, when operating, causes the instrument to carry out the features of an embodiment.

It is clear that the present invention is not limited solely to the above-presented embodiments, but it can be modified within the scope of the appended claims.

The invention claimed is:

1. A micromechanical positioning device, comprising:
   a micromechanical positioning actuator for causing movement of a probe with respect to a target;
   a positioning controller, said positioning controller having an output, said output coupled to said actuator for controlling said movement; and
   said positioning controller having a steering input wherein said steering input is arranged to be coupled to at least one other device over a local communication connection to receive one or more steering signals from said other device, wherein said other device is a micromechanical positioning device, a measurement device or a stimulus device operating on said target, wherein said local communication connection comprises a local communication network for carrying communication messages, wherein said steering input comprises a communications controller operatively connectable to said communication network, wherein said positioning controller is arranged to control said movement based on said steering signals from said other device.

2. The positioning device according to claim 1, further comprising
   a memory for storing positioning control instructions, wherein said positioning control instructions comprise computer-readable positioning logic instructions suitable for use by said positioning controller in controlling said movement based on said steering signals from said other device, wherein said positioning controller is arranged to control said movement based on said steering signals from said other device and said positioning control instructions.

3. The positioning device according to claim 2, wherein said positioning control instructions comprise computer-readable positioning logic instructions, wherein said positioning control instructions suitable for use by said positioning controller in controlling said movement based on sensor signals, wherein said positioning controller is arranged to control said movement based on said steering signals from said other device, said sensor signals, and said positioning control instructions.

4. The positioning device according to claim 3, further comprising an instruction input for receiving said positioning control instructions to said memory from a control unit external to said measurement device.

5. The positioning device according to claim 1, comprising:
a sensor input for said positioning controller, wherein said sensor input is coupled to a sensor for receiving a sensor signal from said sensor to said positioning controller, wherein said positioning controller is arranged to control said movement based on said sensor signal in addition to said steering signals; and
sensor read-out electronics for producing said sensor signal, wherein said sensor read-out electronics is coupled to said sensor and to said sensor input of said positioning controller.

6. The positioning device according to claim 1, further comprising a body having a continuous structure, wherein said body comprises said steering input, said positioning controller, and at least partly said micromechanical positioning actuator.

7. The positioning device according to claim 1, wherein said local communication network is arranged to operate on a multicast or broadcast principle, wherein said positioning device is arranged to listen to multicast or broadcast messages to receive said steering signals.

8. The positioning device according to claim 7, wherein said positioning device is arranged to filter messages and control said movement based on such messages that are determined to be relevant to said positioning device.

9. The positioning device according to claim 1, wherein said communication messages are messages packaged as communication packets for Internet Protocol (IP) transmission, wherein said communication packets carry at least one address and at least one said steering signal, wherein said at least one address identifies at least one positioning device intended to receive said at least one steering signal.

10. The positioning device according to claim 1, comprising:
a steering controller configured to form steering signals for other devices, wherein said other devices are selected from the group consisting of a micromechanical positioning device, a measurement device, or a stimulus device; and
a transmitter configured to transmit said formed steering signals to said other devices over said local communication connection.

11. The positioning device according to claim 10, wherein said steering controller is configured to form a Quality of Service indicator for said steering signals for indicating the priority of said steering signals, wherein said Quality of Service indicator is usable by a communications switch for prioritizing communication messages.

12. The positioning device according to claim 1, further comprising a steering controller configured to decode synchronization steering signals, wherein said synchronization steering signals comprise information on movement of another micromechanical positioning device, wherein said steering controller is configured to control said movement in synchrony with said another micromechanical positioning device according to said synchronization steering signals.

13. A positioning device according to claim 1, comprising:
a plurality of sensors;
at least one micromanipulator actuator for causing movement of at least one sensor with respect to a target;
said positioning controller having a plurality of sensor inputs, said sensor inputs coupled to said sensors for receiving sensor signals from said sensors to said positioning controller; and
said positioning controller arranged to control said movement based on said sensor signals and said steering signals.

14. The positioning device according to claim 1, further comprising a steering controller configured to decode sensor steering signals, wherein said sensor steering signals comprise information on a sensor reading of another device, wherein said steering controller is configured to control said movement according to said sensor steering signals.

15. A control unit for controlling a measurement and positioning system, comprising:
a receiver to receive user input from a user for controlling a measurement;
a memory; and
a processor to determine positioning control instructions based on said received user input, wherein said positioning control instructions comprise computer-readable instructions suitable for use by a positioning controller of a measurement device in controlling movement of a micromechanical positioning actuator based on steering signals from at least one other device over a local communication connection comprising a local communication network for carrying communication messages, wherein said other device is a micromechanical positioning device, a measurement device or a stimulus device operating on said target; and
a transmitter to send said positioning control instructions to at least one positioning device of said measurement and positioning system.

16. The measurement and positioning system comprising a plurality of devices according to claim 15, the control unit being coupled to one or more of said plurality of devices for providing positioning control instructions to said one or more of said plurality of devices.

17. A method for controlling a measurement device, the method comprising:
receiving steering signals from at least one other device over a local communication connection comprising a local communication network for carrying communication messages, wherein said steering signals are received via a steering input of said measurement device to a positioning controller of said measurement device, wherein said other devices are a micromechanical positioning device, a measurement device or a stimulus device operating on said target; and
based on said steering signals from said other device, controlling a movement of a micromechanical positioning actuator causing movement of a probe with respect to a target.

18. A method according to claim 17, the method comprising:
receiving positioning control instructions from a control unit external to said measurement device, said positioning control instructions comprising computer-readable positioning logic instructions suitable for use by said positioning controller in controlling said movement based on said steering signals from said other device;

storing said positioning control instructions in a memory; and controlling said movement based on said steering signals from said other device and said positioning control instructions from said external control unit.

19. A computer program product embodied on a non-transitory computer-readable medium, said computer program product comprising positioning control instructions that, when operated on by a processor, cause a micromechanical positioning device to:

receive steering signals from at least one other device over a local communication connection comprising a local communication network for carrying communication messages, wherein said steering signals are received via a steering input of said measurement device to a positioning controller of said measurement device, wherein said other device is a micromechanical positioning device, a measurement device or a stimulus device operating on said target; and based on said steering signals from said other device, control a movement of a micromechanical positioning actuator causing movement of a probe with respect to a target.

20. A computer program product embodied on a non-transitory computer-readable medium, said computer program product comprising computer code that, when operated on by a processor, cause a control unit of a measurement and positioning system to:

receive, by a receiver, user input from a user for controlling a measurement;

determine, by a processor, positioning control instructions based on said received user input, wherein said positioning control instructions comprise computer-readable positioning logic instructions suitable for use by a positioning controller of a measurement device in controlling movement of a micromechanical positioning actuator based on steering signals from at least one other device over a local communication connection comprising a local communication network for carrying communication messages, wherein said other device is a micromechanical positioning device, a measurement device or a to device operating on said target; and send, by a transmitter, said positioning control instructions to at least one positioning device of said measurement and positioning system.

* * * * *